United States Patent
Burbank et al.

(10) Patent No.: US 6,517,498 B1
(45) Date of Patent: Feb. 11, 2003

(54) APPARATUS AND METHOD FOR TISSUE CAPTURE

(75) Inventors: Fred H. Burbank, Laguna Niguel; William C. Homet, Capistrano Beach; Paul Lubock, Laguna Niguel, all of CA (US)

(73) Assignee: SenoRx, Inc., Aliso Viejo, CA (US)

( * ) Notice: Subject to any disclaimer, the term of this patent is extended or adjusted under 35 U.S.C. 154(b) by 0 days.

(21) Appl. No.: 09/619,867

(22) Filed: Jul. 20, 2000

Related U.S. Application Data (63) Continuation of application No. 09/618,685, filed on Jul. 18, 2000, now abandoned, which is a continuation-in-part of application No. 09/159,467, filed on Sep. 23, 1998, now Pat. No. 6,261,241, and a continuation-in-part of application No. 09/196,125, filed on Nov. 20, 1998, and a continuation-in-part of application No. 09/057,303, filed on Apr. 8, 1998, now Pat. No. 6,331,166.

(60) Provisional application No. 60/076,973, filed on Mar. 3, 1998.

(51) Int. Cl.$^7$ .............................................. A61B 10/00
(52) U.S. Cl. ...................... 600/564; 600/567; 606/45; 606/170
(58) Field of Search ................................ 600/562, 564, 600/566, 567; 606/39, 41, 45–48, 51, 52, 110, 113–115, 167, 170

(56) References Cited

U.S. PATENT DOCUMENTS

| | | | |
|---|---|---|---|
| 2,032,860 A | 3/1936 | Wappler et al. | |
| 3,805,791 A | 4/1974 | Seuberth et al. | |
| 3,847,153 A | 11/1974 | Weissman | 606/45 |
| 3,910,279 A | 10/1975 | Okada et al. | |
| 3,955,578 A | 5/1976 | Chamness et al. | |
| 4,202,338 A | 5/1980 | Bitroff | |
| 4,243,048 A | 1/1981 | Griffin | |

(List continued on next page.)

FOREIGN PATENT DOCUMENTS

| | | |
|---|---|---|
| DE | 19528440 A1 | 8/1995 |
| EP | 0472368 A2 | 8/1991 |
| EP | 0509670 A | 10/1992 |
| EP | 0 509 670 A2 | 10/1992 |
| EP | 0667126 | 8/1995 |
| GB | 2311468 A | 2/1997 |
| WO | 9313718 | 7/1993 |
| WO | WO 95/02370 | 7/1994 |
| WO | WO 95/02371 | 7/1994 |
| WO | 95/02370 | 1/1995 |
| WO | 95/02371 | 1/1995 |
| WO | 98/08441 | 3/1998 |
| WO | 98/43531 | 10/1998 |
| WO | WO 00/16697 | 3/2000 |

OTHER PUBLICATIONS

Armstrong J.S. et al., "Differential marking of excision planes in screened breast lesions by orgnically coloured gelantins [see comments].", *Journal of Clinical Pathology*, (Jul. 1990), 43(7) 604–7, XP000971447 abstract; tables 1 and 2.

(List continued on next page.)

*Primary Examiner*—Kevin Shaver
*Assistant Examiner*—Charles Marmor, II
(74) *Attorney, Agent, or Firm*—Coudert Brothers LLP (57) ABSTRACT

A tissue acquisition system includes electrodes that are energized by a radio frequency (RF) energy source. Retractable electrodes are energized and extended from a cannula and the cannula is advanced in the tissue to position the cannula near the target tissue site in a patient. The retractable electrodes are then retracted and a distal electrode cuts a tissue sample from the tissue site when the cannula is further advanced into the tissue. The retractable electrodes are then energized and extended from the cannula and the cannula is rotated to separate the tissue sample from the tissue site. The tissue sample is ejected through the cannula for collection by advancing a dilator.

26 Claims, 11 Drawing Sheets

U.S. PATENT DOCUMENTS

| Patent | Date | Name | Ref |
|---|---|---|---|
| 4,294,254 A | 10/1981 | Chamness | |
| 4,311,143 A | 1/1982 | Komiya | |
| 4,362,160 A | 12/1982 | Hiltebrandt | |
| 4,418,692 A | 12/1983 | Guay | 606/42 |
| 4,503,855 A | 3/1985 | Maslanka | |
| 4,565,200 A | 1/1986 | Cosman | |
| 4,576,162 A | 3/1986 | McCorkle | |
| 4,638,802 A | 1/1987 | Okada | |
| 4,718,419 A | 1/1988 | Okada | |
| 4,724,836 A | 2/1988 | Okada | |
| 5,007,908 A | 4/1991 | Rydell | |
| 5,024,617 A | 6/1991 | Karpiel | |
| 5,035,696 A | 7/1991 | Rydell | |
| 5,047,027 A * | 9/1991 | Rydell | 606/48 |
| 5,064,424 A | 11/1991 | Bitrolf | |
| 5,066,295 A | 11/1991 | Kozak et al. | |
| 5,078,716 A | 1/1992 | Doll | |
| 5,080,660 A | 1/1992 | Buelna | |
| RE,033,925 E | 5/1992 | Bales et al. | |
| 5,111,828 A | 5/1992 | Kornberg et al. | 600/567 |
| 5,133,359 A | 7/1992 | Kedem | |
| 5,133,360 A | 7/1992 | Spears | |
| RE,034,056 E | 9/1992 | Lindgren et al. | |
| 5,158,561 A | 10/1992 | Rydell et al. | |
| 5,163,938 A | 11/1992 | Kambara et al. | |
| 5,196,007 A | 3/1993 | Ellman et al. | |
| 5,201,732 A | 4/1993 | Parins et al. | |
| 5,201,741 A | 4/1993 | Dulebohn | |
| 5,207,686 A | 5/1993 | Dolgin | |
| 5,224,488 A | 7/1993 | Neuffer | |
| 5,258,006 A | 11/1993 | Rydell et al. | 606/205 |
| 5,281,218 A | 1/1994 | Imran | |
| 5,312,400 A | 5/1994 | Bales et al. | |
| 5,318,564 A | 6/1994 | Eggers | |
| 5,323,768 A | 6/1994 | Saito et al. | |
| 5,324,288 A | 6/1994 | Billings et al. | |
| 5,330,471 A | 7/1994 | Eggers | 606/48 |
| 5,335,671 A | 8/1994 | Clement | |
| 5,344,420 A | 9/1994 | Hilal et al. | |
| 5,376,094 A | 12/1994 | Kline | |
| 5,380,321 A | 1/1995 | Yoon | |
| 5,395,312 A | 3/1995 | Desai | |
| 5,401,272 A | 3/1995 | Perkins | 606/15 |
| 5,415,656 A | 5/1995 | Tihon et al. | |
| 5,417,687 A * | 5/1995 | Nardella et al. | 606/45 |
| 5,417,697 A | 5/1995 | Wilk et al. | |
| 5,423,814 A | 6/1995 | Zhu et al. | |
| 5,431,649 A | 7/1995 | Mulier et al. | |
| 5,437,665 A | 8/1995 | Munro | |
| 5,441,498 A * | 8/1995 | Perkins | 606/15 |
| 5,441,503 A | 8/1995 | Considine et al. | 606/115 |
| 5,462,553 A | 10/1995 | Dolgin | |
| 5,470,308 A | 11/1995 | Edwards et al. | |
| 5,477,862 A | 12/1995 | Haga | |
| 5,484,436 A | 1/1996 | Eggers et al. | |
| 5,501,654 A | 3/1996 | Failla et al. | |
| 5,526,822 A | 6/1996 | Burbank et al. | |
| 5,527,331 A | 6/1996 | Kresch et al. | |
| 5,536,267 A | 7/1996 | Edwards et al. | 606/41 |
| 5,542,948 A | 8/1996 | Weaver et al. | |
| 5,611,803 A | 3/1997 | Heaven et al. | |
| 5,643,282 A | 7/1997 | Kieturakis | |
| 5,649,547 A | 7/1997 | Ritchart et al. | |
| 5,665,085 A | 9/1997 | Nardella | |
| 5,672,174 A | 9/1997 | Gough et al. | 606/41 |
| 5,674,184 A | 10/1997 | Hassler, Jr. | |
| 5,687,739 A | 11/1997 | McPherson et al. | |
| 5,715,825 A | 2/1998 | Crowley | |
| 5,741,225 A | 4/1998 | Lax et al. | |
| 5,766,169 A | 6/1998 | Fritzsch et al. | 606/48 |
| 5,769,086 A | 6/1998 | Richart et al. | |
| 5,775,333 A | 7/1998 | Burbank et al. | |
| 5,782,775 A | 7/1998 | Milliman et al. | |
| 5,782,827 A * | 7/1998 | Gough et al. | 606/41 |
| 5,794,626 A | 8/1998 | Kieturakis | |
| 5,797,907 A | 8/1998 | Clement | |
| 5,810,806 A | 9/1998 | Ritchart et al. | 606/45 |
| 5,882,316 A | 3/1999 | Chu et al. | |
| 5,902,272 A | 5/1999 | Eggers et al. | |
| 5,913,857 A * | 6/1999 | Ritchart et al. | 606/45 |
| 5,928,164 A | 7/1999 | Burbank et al. | |
| 5,938,587 A * | 8/1999 | Taylor et al. | 600/139 |
| 5,947,964 A | 9/1999 | Eggers et al. | |
| 6,036,681 A * | 3/2000 | Hooven | 604/506 |
| 6,050,992 A * | 4/2000 | Nichols | 606/41 |
| 6,059,782 A | 5/2000 | Novak et al. | 606/48 |
| 6,063,082 A | 5/2000 | DeVore et al. | 606/45 |
| 6,071,280 A * | 6/2000 | Edwards et al. | 606/41 |
| 6,120,462 A | 9/2000 | Hibner et al. | |
| 6,277,083 B1 * | 8/2001 | Eggers et al. | 600/564 |

OTHER PUBLICATIONS

Blackwell Science Ltd., "The Loop Electrode: a New Device for US–guided Interstitial Tissue Ablation Using Radio frequency Electrosurgery –An Animal Study" *Min Incas Ther & Allied Technol*, pp. 5.511–516 (1996).

English translation of German Application DE 195 28 440 A1, published Aug. 2, 1995.

Micklos, Timothy J. "Percutaneous Biopsy Techniques" *Manual of Oncologic Therapeutics* (1989/1990) pp. 39–42.

Whitman et al. "Coaxial Core Needle Biopsy Under Mammographic Guidance: Indications and Applications" AJR:171, Jul. 1998, pp. 67–70.

International Search report for PCT/US99/21416, mailed May 19, 2000.

International Search report for PCT/US01/22894, mailed Nov. 21, 2001.

Written Opinion for PCT/US99/21416, mailed Jul. 18, 2000.

Burbank, F., M.D., "Stereotactic Breast Biopsy: Its History, Its Present, and Its Future", *The American Surgeon*, Feb. 1996, vol. 62, pp. 128–150.

* cited by examiner

APPARATUS AND METHOD FOR TISSUE CAPTURE

RELATED APPLICATIONS

This application claims priority from and is a continuation of U.S. application Ser. No. 09/618,685, filed Jul. 18, 2000, by Homet et al. now abandoned, which is a continuation-in-part of U.S. application Ser. No. 09/159,467, filed Sep. 23, 1998, by Burbank et al. now U.S. Pat. No. 6,261,241 and co-pending U.S. application Ser. No. 09/196,125, filed Nov. 20, 1998, by Burbank et al., and U.S. application Ser. No. 09/057,303, filed Apr. 8, 1998, by Burbank et al. now U.S. Pat. No. 6,331,166, which claims priority from U.S. Provisional Application Serial No. 60/076,973, filed Mar. 3, 1998 by Burbank et al. All of the aforementioned applications are hereby incorporated by reference in their entirety.

BACKGROUND

At times it is necessary to sample or remove a portion of tissue from humans or animals in the diagnosis and treatment of patients with suspicious lesions or areas of tissue, whether they are cancerous or malignant. If the patient has cancer, such as cancer of the breast, there is an advantage for early detection and diagnosis through the use of screening techniques, such as physical examination, or mammography. Mammography is capable of detecting small abnormalities, which are often not palpable during physical examination. A physician determines through mammography, ultrasound or other screening techniques when a biopsy must be performed. A biopsy may be performed by an open or percutaneous technique. Open biopsy is an invasive surgical procedure involving cutting into the suspicious tissue and directly visualizing the target area to remove the entire mass or a part of the mass. Percutaneous biopsy is usually done with a needle-like instrument through a small incision performed with the aid of an imaging device such as X-ray, ultrasound, MRI or the like, and may utilize either a fine needle aspiration or a core biopsy. Core biopsy is extremely useful in a number of conditions and is being used more frequently by the medical profession.

To arrive at a definitive tissue diagnosis, intact tissue is needed from an organ or lesion within the body. In most instances, only part of the organ or lesion need be sampled. However, the portions of tissue obtained must be representative of the organ or lesion as a whole. In the past, to obtain tissue from organs or lesions within the body, surgery had to be performed to locate, identify and remove the tissue. With the advent of medical imaging equipment (X-rays and fluoroscopy, computed tomography, ultrasound, nuclear medicine, and magnetic resonance imaging) it became possible to identify small abnormalities even deep within the body. However, definitive tissue characterization still requires obtaining adequate tissue samples to characterize the histology of the organ or lesion.

For example, mammography can identify non-palpable (not perceptible by touch) breast abnormalities earlier than they can be diagnosed by physical examination. Most non-palpable breast abnormalities are benign; some of them are malignant. When breast cancer is diagnosed before it becomes palpable, breast cancer mortality can be reduced. However, it is often difficult to determine if pre-palpable breast abnormalities are malignant, as some benign lesions have mammographic features which mimic malignant lesions and some malignant lesions have mammographic features which mimic benign lesions. Thus, mammography has its limitations. To reach a definitive diagnosis, tissue from within the breast must be removed and examined under a microscope. Prior to the late 1980's, reaching a definitive tissue diagnosis for non-palpable breast disease required a mammographically guided localization, either with a wire device, visible dye, or carbon particles, followed by an open, surgical biopsy utilizing one of these guidance methods to lead the surgeon to the non-palpable lesion within the breast.

One type of image-guided breast biopsy instrument currently available is a vacuum-assisted automatic core biopsy device. One such successful biopsy device is shown and disclosed in U.S. Pat. No. 5,526,822 to Burbank et al, which is expressly incorporated by reference herein. This device, known commercially as the MAMMOTOME™ Biopsy System, which is available from Ethicon Endo-Surgery, Inc., a division of Johnson & Johnson, has the capability to actively capture tissue prior to cutting the tissue. Active capture allows for sampling through non-homogeneous tissues. The device is comprised of a disposable probe, a motorized drive unit, and an integrated vacuum source. The probe is made of stainless steel and molded plastic and is designed for collection of multiple tissue samples with a single insertion of the probe into the breast. The tip of the probe is configured with a laterally-disposed sampling notch for capturing tissue samples. Orientation of the sample notch is directed by the physician, who uses a thumbwheel to direct tissue sampling in any direction about the circumference of the probe. A hollow cylindrical cutter severs and transports the tissue samples to a tissue collection chamber for later testing.

Co-pending U.S. patent application Ser. No. 09/057,303, which is expressly incorporated by reference herein, discloses apparatuses and methods for precisely isolating a target lesion, resulting in a high likelihood of "clean" margins about the lesion. This advantageously will often result in the ability to both diagnose and treat a malignant lesion with only a single percutaneous procedure, with no follow-up percutaneous or surgical procedure required, while minimizing the risk of migration of possibly cancerous cells from the lesion to surrounding tissue or the bloodstream. Various tissue acquisition instrument embodiments are disclosed for segmenting the target tissue, including embodiments wherein the instrument comprises a cutting element which is extendable radially outwardly and movable circumferentially to define a peripheral margin about a tissue sample, and other embodiments wherein the cutting element is extendable radially outwardly and movable axially to define peripheral margins about the tissue sample.

Co-pending U.S. patent application Ser. No. 09/196,125, which is expressly incorporated by reference herein, discloses tissue acquisition systems and methods that include radio frequency (RF) cutter loops which are extendable out of a cannula to cut cylindrical tissue samples from a tissue of interest in a patient. The cannula includes inner and outer cannulae which are mutually rotatable and include cutouts through which the cutting loop can be rotated and longitudinally extended to perform the cuts. The tissue samples are then aspirated proximally through the cannula for collection.

SUMMARY

According to a first exemplary embodiment of the present invention a tissue acquisition device useful in retrieving tissue samples from a patient comprises a cannula that has a longitudinal axis and a lumen extending along the longitudinal axis and a distally located electrode that has a lumen that is coaxially aligned with the cannula lumen, the electrode is fixedly attached to and is located adjacent to the cannula.

According to a second exemplary embodiment of the present invention, a system for sampling tissue from a patient comprises a RF energy generator capable of generating RF energy and a tissue acquisition device that includes a cannula that has a longitudinal axis and a lumen extending along the longitudinal axis and a distally located electrode that has a lumen that is coaxially aligned with the cannula lumen, the electrode is fixedly attached to and is located adjacent to the cannula and is in electrical communication with the RF energy generator.

According to the third exemplary embodiment of the present invention, a method of sampling tissue from a patient comprises the steps of inserting a cannula into tissue of a patient, the cannula includes an electrode coaxially aligned with and fixedly attached to the cannula, and separating the tissue by advancing the cannula through the tissue of a patient.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to specific embodiments of the apparatus and method, given only by way of example, and with reference to the accompanying drawings.

DETAILED DESCRIPTION

Figure 1:
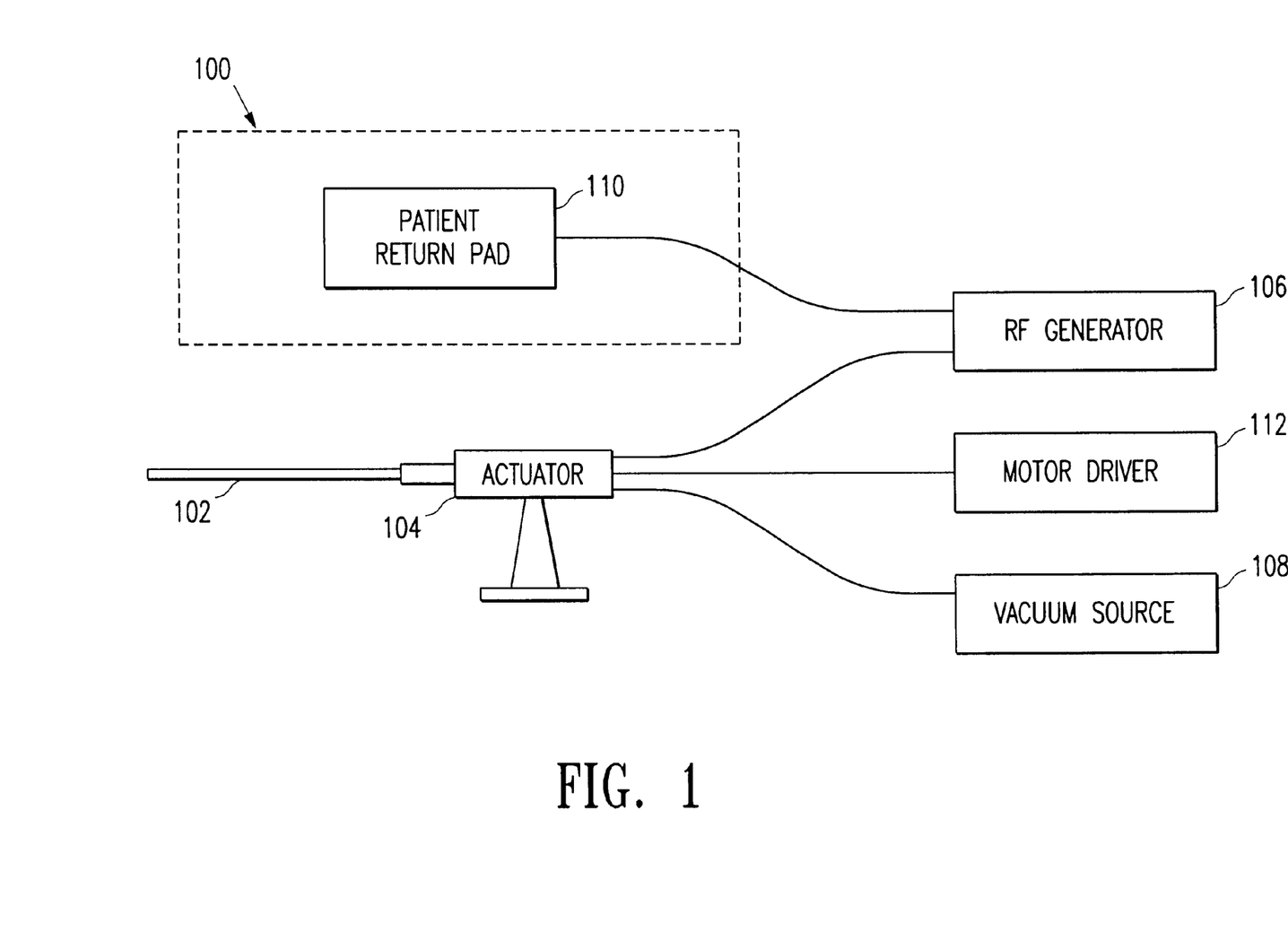
FIG. 1 is a schematic illustration of a tissue acquisition system according to the present invention.

Referring to the drawing figures, like reference numerals designate identical or corresponding elements throughout the several figures. In FIG. 1, a system 100 for sampling or removing tissue from a patient (not illustrated), includes a cannula assembly 102, which is preferably constructed of materials so that it can economically be disposable. System 100 further includes an actuator 104 to which cannula assembly 102 is removably attached. Actuator 104 is preferably non-disposable or constructed of materials and includes components which are intended to be reused. Actuator 104 is the interface between cannula assembly 102 and an RF generator 106 and an optional vacuum source 108. The actuator 104 also includes at least one motor (not illustrated), which extends and retracts a pair of retractable electrodes (see FIGS. 5 and 6) from the cannula assembly 102. Additionally, actuator 104 includes switches and proximity sensors which provide control signals for controlling the motor, RF generator 106, and vacuum source 108.

Actuator 104 is connected to and in electrical communication with RF generator 106, which is connected to and in electrical communication with a patient return pad 110 for the RF cutting, or tissue separating system, described in greater detail below. The switches in actuator 104 (not illustrated) control the application of RF energy to the cannula assembly 102, as described in greater detail below. The RF generator 106 can be activated by a footswitch or other means and typically operates at about 200 to about 1000 KHz, specifically, about 300 to about 900 KHz, and more specifically about 330 to about 500 KHz. Power output for the RF generator 106 can be about 50 to about 150 Watts, more specifically, about 80 to about 100 Watts. However, it will be realized that an RF generator 106 exhibiting a wide variety of output parameters would be suitable. A motor driver 112 is also connected to actuator 104, and provides power to the motors in actuator 104. Motor driver 112 receives signals from the switches and proximity sensors in actuator 104, which are used as feedback control signals to control the states of the motors. Vacuum source 108 is optional and includes a vacuum pump or other suitable source of vacuum (not illustrated), and is controllable to at least two vacuum pressure levels. The vacuum pump can also be controllable over a continuum of pressure levels.

As shown in FIGS. 2–7, the cannula assembly 102 includes a cannula 116, a pair of opposing retractable electrodes 118 and 120 that generally extend along the length of the cannula 116, a distally located electrode 122 (a distal electrode that is supported by a pair of distal electrode supports 124 and 126 that generally extend the length of the cannula 116), an electrical input block 128, and an electrically nonconductive sheath 130. The sheath 130 extends from a cannula proximal end 132 to a cannula distal end 134 and compressively covers and holds the pair of retractable electrodes 118 and 120 and the pair of distal electrode supports 124 and 126 against the cannula 116. Although a pair of distal electrode supports are shown, a single distal electrode support may be utilized.

Figure 2:
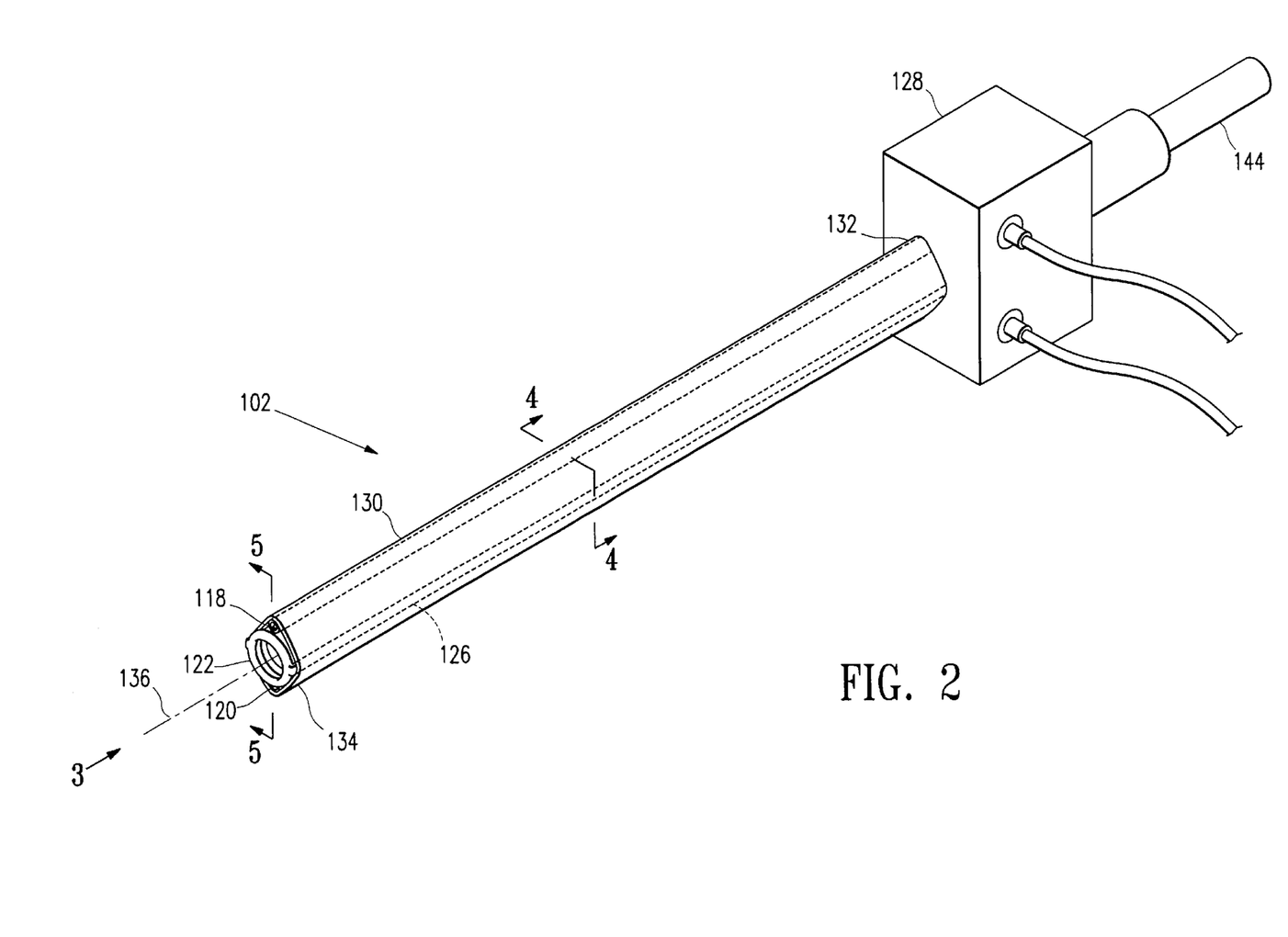
FIG. 2 is a perspective view of a cannula assembly according to the present invention with a dilator retracted.
Figure 3:
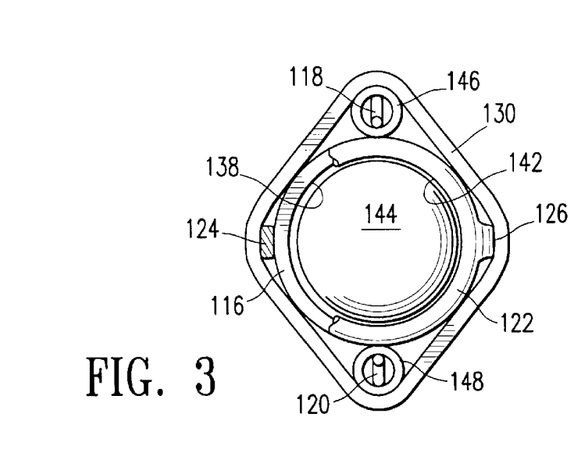
FIG. 3 is an elevational distal end view taken at arrow 3 in FIG. 2 of the cannula assembly illustrated in FIG. 2.
Figure 4:
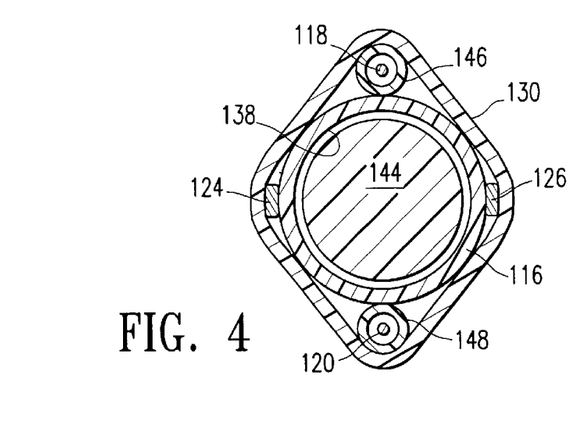
FIG. 4 is a cross-sectional view taken at line 4—4 in FIG. 2 of the cannula assembly illustrated in FIG. 2.

The cannula 116 is generally tubular and has a longitudinal axis 136 that extends between the proximal end 132 and the opposite distal end 134. The cannula 116 has a tissue lumen 138 that extends longitudinally from the proximal end 132 to the distal end 134. The cannula 116 is preferably formed of a relatively rigid, electrically non-conductive, and biocompatible material. The cannula 116 is optionally provided with a lubricious coating on the inner surface and the outer surface of the cannula 116, which allows a tissue sample to be more easily drawn along the tissue lumen 138. The cannula 116 can be formed of an electrically insulating biocompatible material, such as a medical grade polymer like polycarbonate. The cannula 116 can have a length of about 3 to about 15 cm, more specifically, about 5 to about 13 cm, and even more specifically, about 8 to about 9 cm. In one embodiment, the cannula 116 can have an inside transverse dimension or diameter of about 3 to about 10 mm, more specifically, about 5 to about 7 mm.

The distal electrode 122 is fixedly attached to and is located distally of the cannula 116 approximate to the cannula distal end 134 to define a gap 140 between the distal electrode 122 and the cannula 116. The distal electrode 122 has a lumen 142 that has the same geometric cross sectional shape as the tissue lumen 138 and is coaxially aligned with the tissue lumen 138 so as to have the same longitudinal axis 136. In the example shown, the lumen 142 and the tissue lumen 138 each have a generally circular cross sectional shape when taken perpendicular to the longitudinal axis 136. The distal electrode 122 is supported by the first distal electrode support 124 and the opposing second distal electrode support 126. The electrode supports 124 and 126 extend from the proximal end 132 to the distal end 134 and are located externally of the cannula 116 approximately 180 degrees apart from each other. The electrode supports 124 and 126, as well as the distal electrode 122, are electrically connected to the electrical input block 128 for the input of RF energy.

A dilator 144 is movably positioned in the tissue lumen 138 for ejecting a tissue sample 162, once obtained, from the cannula 116. The distal end of the dilator 144 is generally convex, so that it bulges out from the dilator 144 to help push the tissue sample 162 out of the tissue lumen 138. The dilator 144, as explained below, is positioned distally while inserting the cannula assembly to the tissue sample location, which provides a separating traction force to the tissue while it is being separated.

Figure 5:
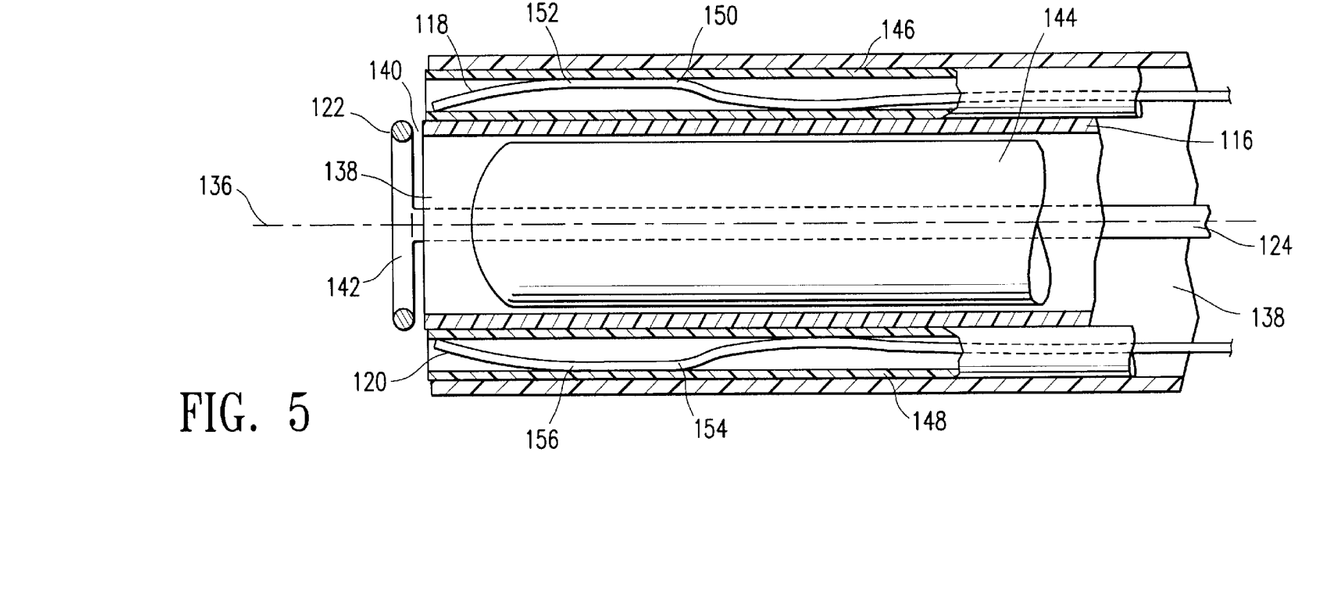
FIG. 5 is a cross-sectional view taken at line 5—5 in FIG. 2 of the cannula assembly illustrated in FIG. 2, showing a pair of opposing retractable electrodes in a retracted position.
Figure 6:
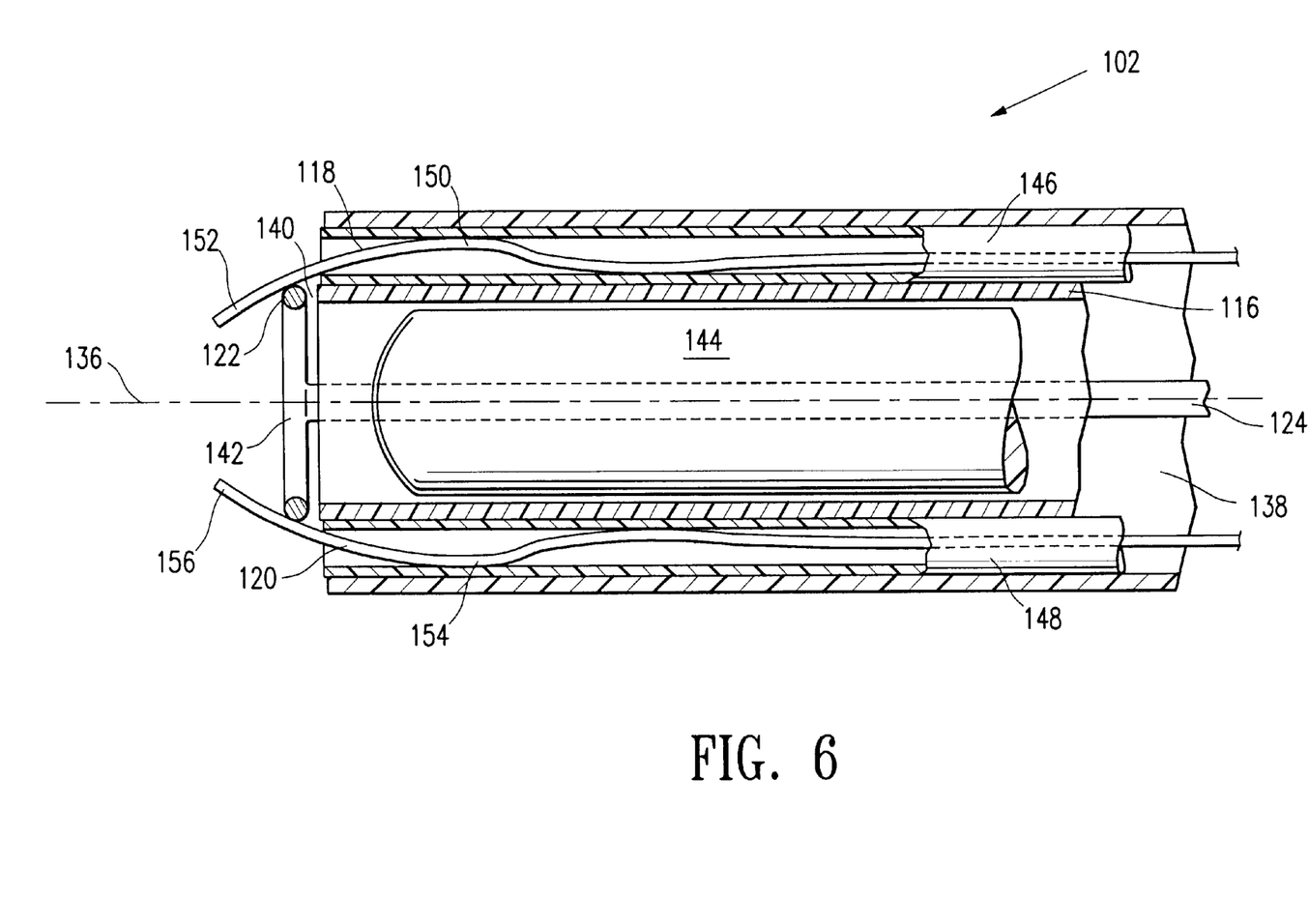
FIG. 6 is a cross-sectional view of the cannula assembly illustrated in FIG. 2, showing the pair of opposing retractable electrodes in a partially extended position.
Figures 6A, 6B:
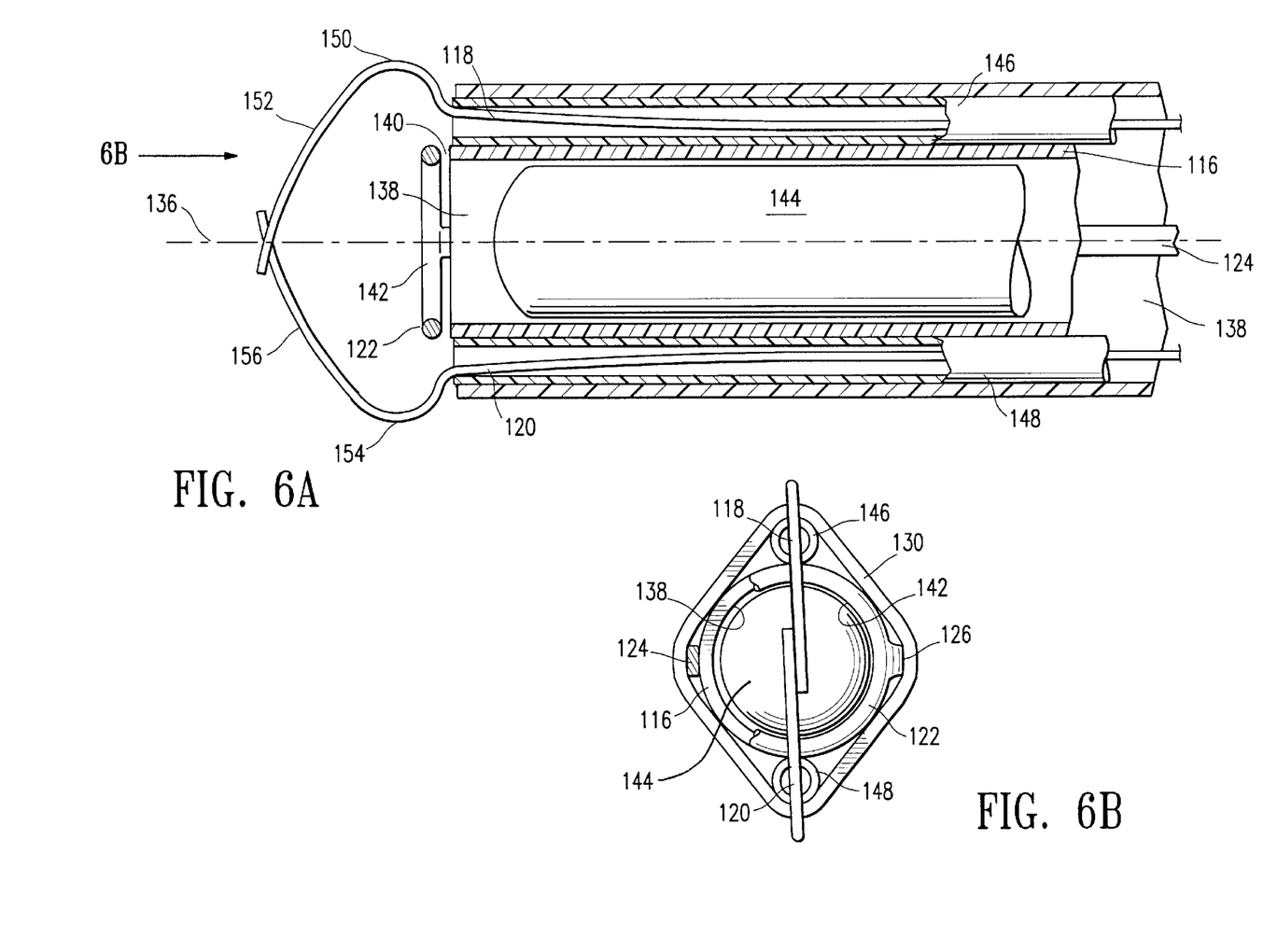
FIG. 6A shows an elevational view in partial longitudinal section of the cannula assembly.
FIG. 6B is an end view of the cannula assembly taken at arrow 6B shown in FIG. 6A.

The retractable electrodes 118 and 120 generally extend from the proximal end 132 to the distal end 134 and are located externally of the cannula 116 approximately 180 degrees apart from each other and approximately 90 degrees apart from the electrode supports 124 and 126. The first retractable electrode 118 is housed in a first housing 146 and likewise, the second retractable electrode 120 is housed in a second housing 148. The housings 146 and 148 are generally tubular in shape to accommodate the retractable electrodes 118 and 120, which are slidably positioned in the respective housings. The retractable electrodes 118 and 120 are electrically connected to the electrical input block 128 for the input of RF energy. The housings 146 and 148 extend from the proximal end 132 to the distal end 134, but do not extend beyond the gap 140. When the retractable electrodes 118 and 120 are retracted into the housings 146 and 148 respectively, the retractable electrodes 118 and 120 do not extend distally beyond the housings and are generally parallel to the longitudinal axis 136.

The retractable electrodes 118 and 120 each are pre-stressed, or pre-bent so that as the retractable electrodes 118 and 120 have a first configuration when retracted in the housings and a second configuration when extended from the housings. When the retractable electrodes 118 and 120 are extended from the electrode housings 146 and 148 respectively, the retractable electrodes 118 and 120 follow a desired path.

Figure 7:
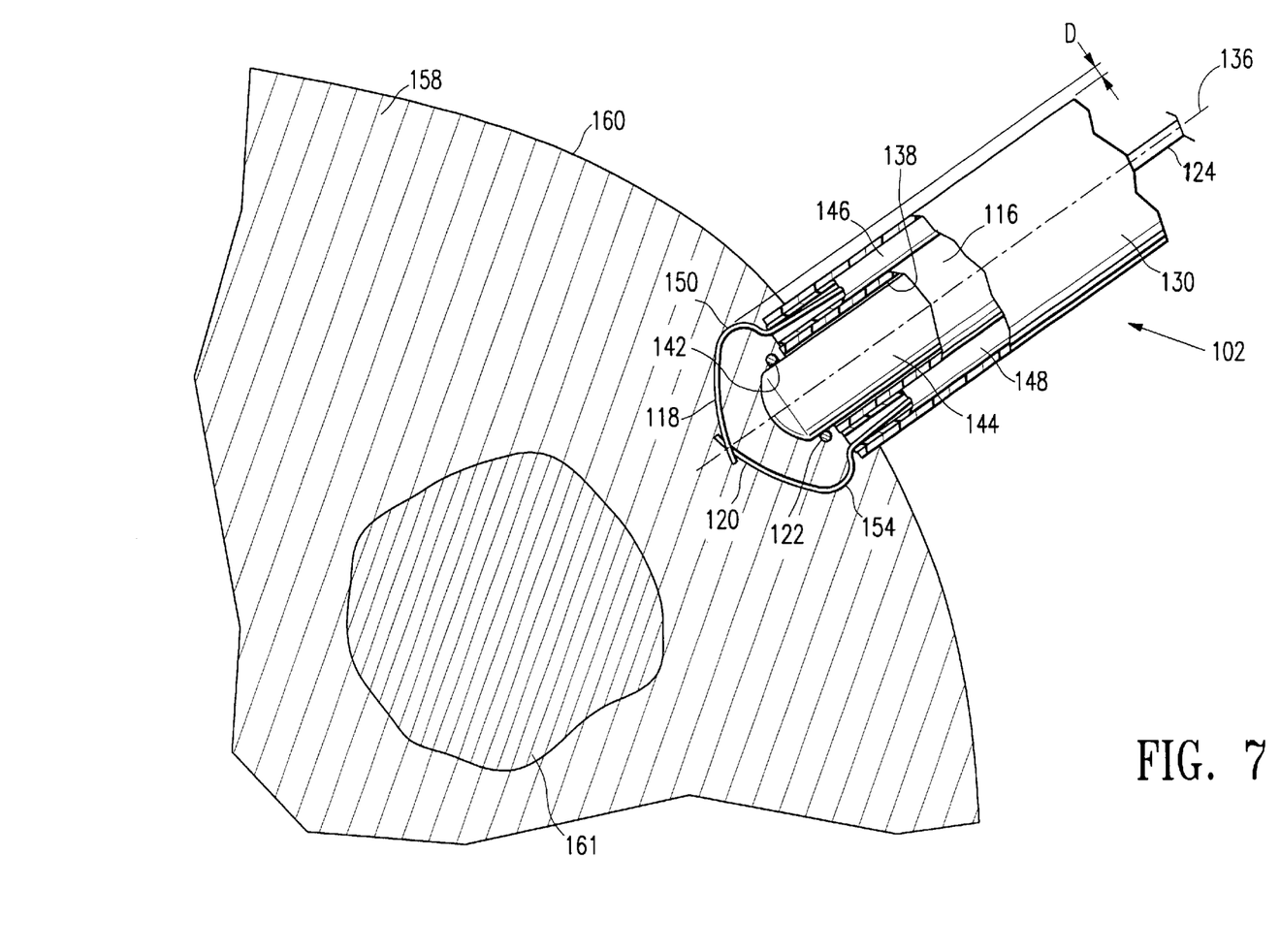
FIG. 7 is a cross-sectional view of the cannula assembly illustrated in FIG. 2, showing the dilator distally positioned and a pair of opposing retractable electrodes in a fully extended position and positioned in a skin incision and in the tissue of a patient.

As shown in FIGS. 5–7, the first retractable electrode 118 has an outwardly biased first apex 150 and a first distally located portion 152. Likewise, the second retractable electrode 120 is a mirror image of the first retractable electrode 118 with an outwardly biased second apex 154 and a second distally located portion 156. As the retractable electrodes 118 and 120 are extended from the respective housings 146 and 148, the distally located portions 152 and 156 approach the longitudinal axis 136. When the retractable electrodes 118 and 120 are fully extended from the respective housings 146 and 148, the distally located portions 152 and 156 intersect and overlap or cross the longitudinal axis 136 and each other. In addition, when the retractable electrodes 118 and 120 are fully extended from the respective housings 146 and 148, the apexes 150 and 154 extend radially beyond the outer surfaces of the cannula 116 and the cannula assembly 102 by a dimension D so that the cannula assembly 102 may be inserted into an incision made or augmented by the retractable electrodes 118 and 120. The extension of the retractable electrodes 118 and 120 to dimension D can compensate for the circumference of the cannula assembly 102 so that the transverse dimension of the retractable electrodes 118 and 120 in their extended position can be about one half the circumference of the cannula 116. Generally, the greater the magnitude of dimension D, the more easily the cannula assembly 102 will follow an incision or channel made by activated or energized retractable electrodes 118 and 120 when inserted into tissue.

The distal electrode 122 and the retractable electrodes 118 and 120 are formed of a conductive material so that the electrodes can be used as a RF energy cutting, or separating electrode. Preferably, the electrodes are formed of stainless steel, tungsten, platinum, or titanium alloy wire. The electrodes 118, 120 and 122 can be made from wire having a transverse dimension or diameter of about 0.002 to about 0.015 inch, more specifically, about 0.004 to about 0.01 inch, and even more specifically, about 0.006 to about 0.008 inch.

In use, an optional incision is made in the skin of the patient at the body surface 160 with a scalpel or similar instrument. The retractable electrodes 118 and 120 are fully extended, as shown in FIG. 7, and positioned within the incision made with the scalpel. RF energy is applied to the retractable electrodes, and the cannula assembly 102 is advanced into the patient's tissue by pressing the cannula assembly 102 into the body surface 160 and into the tissue 158. Optionally, RF energy from RF generator 106 can pass through the first and second distal electrode supports 124 and 126, which act as electrical conductors, to the distal electrode 122 during penetration of the cannula assembly into the patient's tissue.

The dilator 144 can be positioned through the lumen 142 and extends distally out of the cannula assembly 102 during penetration into the tissue. The dilator 144 provides traction to the tissue and helps to separate the tissue during the insertion step. The dilator 144 is retracted during or prior to the tissue sampling step. The distal electrode 122 is advanced into the incision and into the tissue, which allows the cannula assembly 102 to advance into the tissue 158 and to a site at which a tissue sample is desired with a minimum amount of trauma to the patient.

The use of the retractable electrodes 118 and 120 to get to the site and use of the distal electrode 122 is also advantageous because the RF cutting, or separating which is provided therewith allows entry of the cannula assembly 102 into the target tissue with much less pushing force than prior devices, and in particular than prior devices which rely on a sharpened or pointed cannula for entry into the target tissue. In addition, there is less deflection of the cannula assembly 102 when compared to prior devices since the distal electrode 122 easily separates different tissue that is adjacent to each other. For example, adjacent fatty, glandular, and lesion tissue would typically cause the prior devices to deflect as the device passes from one tissue to the next; however, the distal electrode 122 of the present invention easily separates adjacent varying tissue with the RF energized electrode 122.

Figure 8:
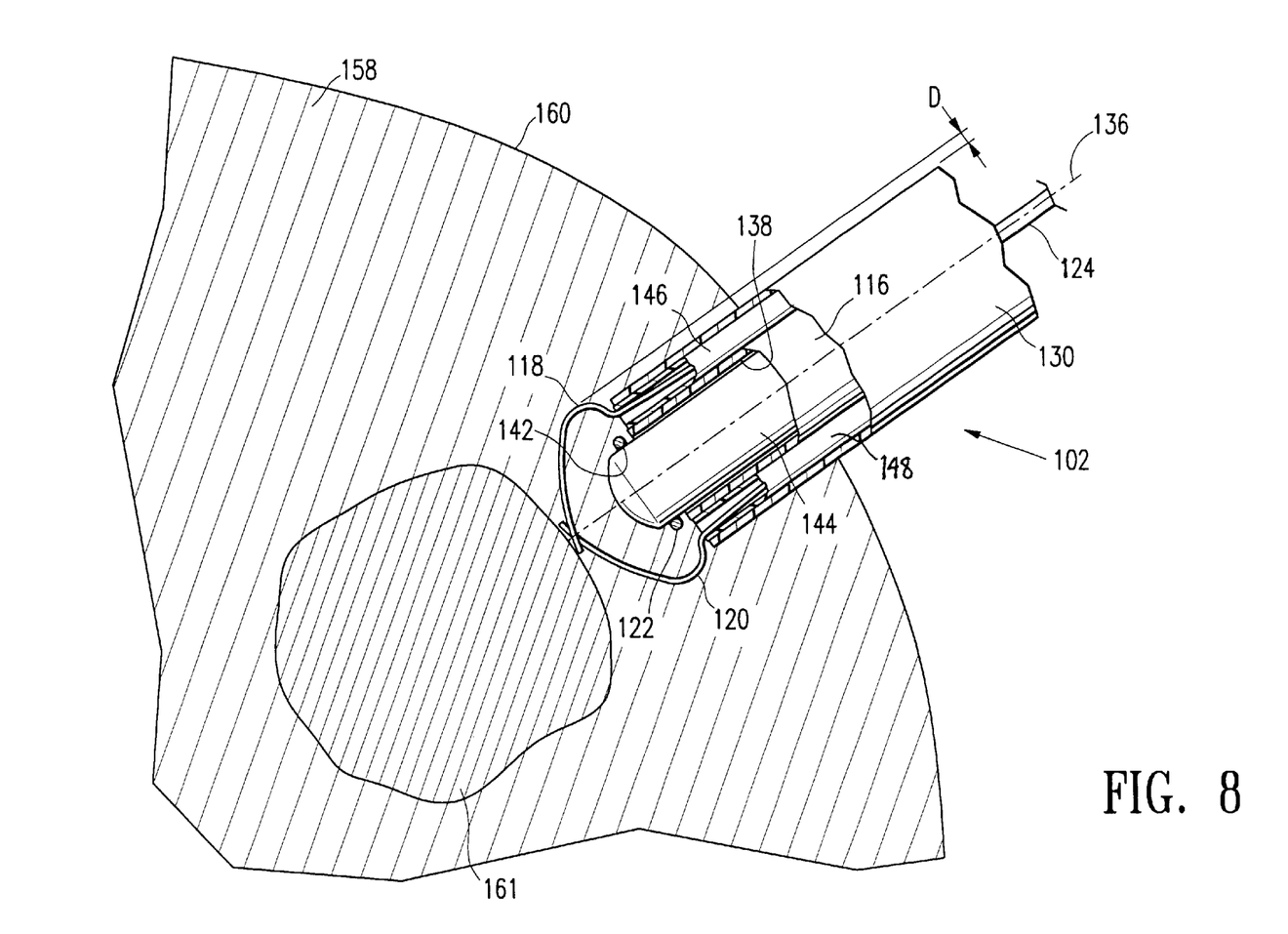
FIG. 8 is a cross-sectional view of the cannula assembly illustrated in FIG. 7, showing the pair of opposing retractable electrodes in the extended position and the cannula assembly positioned further inside of the tissue of the patient.
Figure 9:
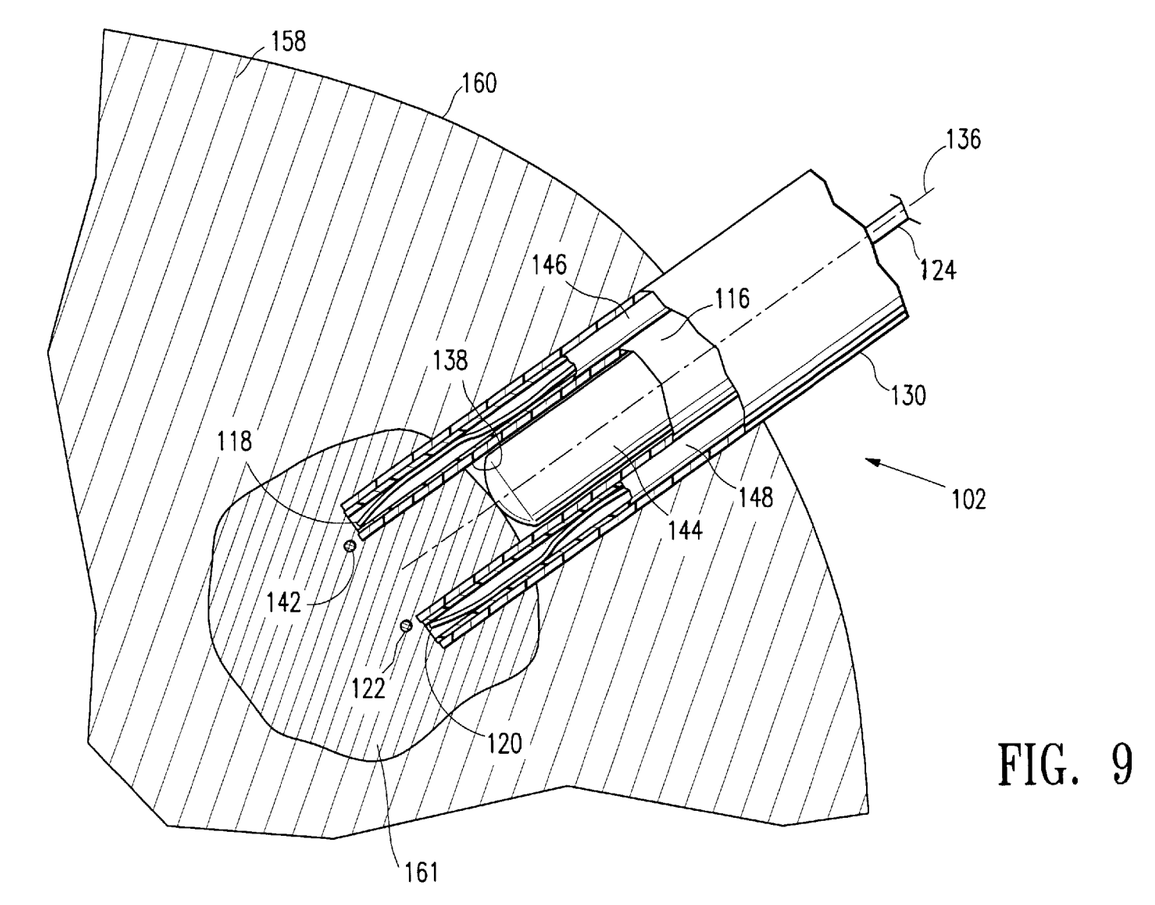
FIG. 9 is a cross-sectional view of the cannula assembly illustrated in FIG. 2, showing the pair of opposing retractable electrodes in the retracted position and the cannula assembly positioned inside of the tissue of the patient with a tissue sample located in the cannula assembly adjacent to the dilator.

A method of operating the above-described apparatus for collecting tissue samples will now be described with reference to FIGS. 7–12. The region of the tissue from which the sample is to be drawn is located. The retractable electrodes 118 and 120 are then extended and energized with RF energy. The cannula assembly 102 is then positioned adjacent to the tissue region of interest. With the aid of ultrasound, palpation, MRI, stereotactic X-ray equipment or other imaging devices, the cannula assembly 102 is advanced through the body surface 160 and through the tissue 158 to the lesion 161, as shown in FIGS. 7 and 8. The retractable electrodes 118 and 120 are then de-energized and retracted. As shown in FIG. 9, the distal electrode 122 is then energized with RF energy, which allows the cannula assembly 102 to be easily advanced into the tissue 158 to the target site 161. The dilator 144 is pushed back by the tissue or is retracted from the cannula 116 while the cannula assembly 102 is advanced to create a vacuum in the cannula 116.

As the cannula assembly 102 is advanced a tissue channel is created and a tissue sample 162 is captured in the tissue lumen 138 of the cannula 116. Before the advancement of the cannula assembly 102 into the tissue, the optional vacuum source is activated to begin drawing tissue close to the tissue lumen 138. If it is necessary to draw the tissue closer to the tissue lumen 138, the vacuum source 108 can be adjusted to increase the negative pressure applied through tissue lumen 138. As the vacuum source is applied to the tissue lumen 138, the tissue sample 162 is drawn into the tissue lumen 138 of the cannula 116, beginning with the proximal end thereof. At this point, the tissue sample 162 is still connected to the tissue mass.

Figure 10:
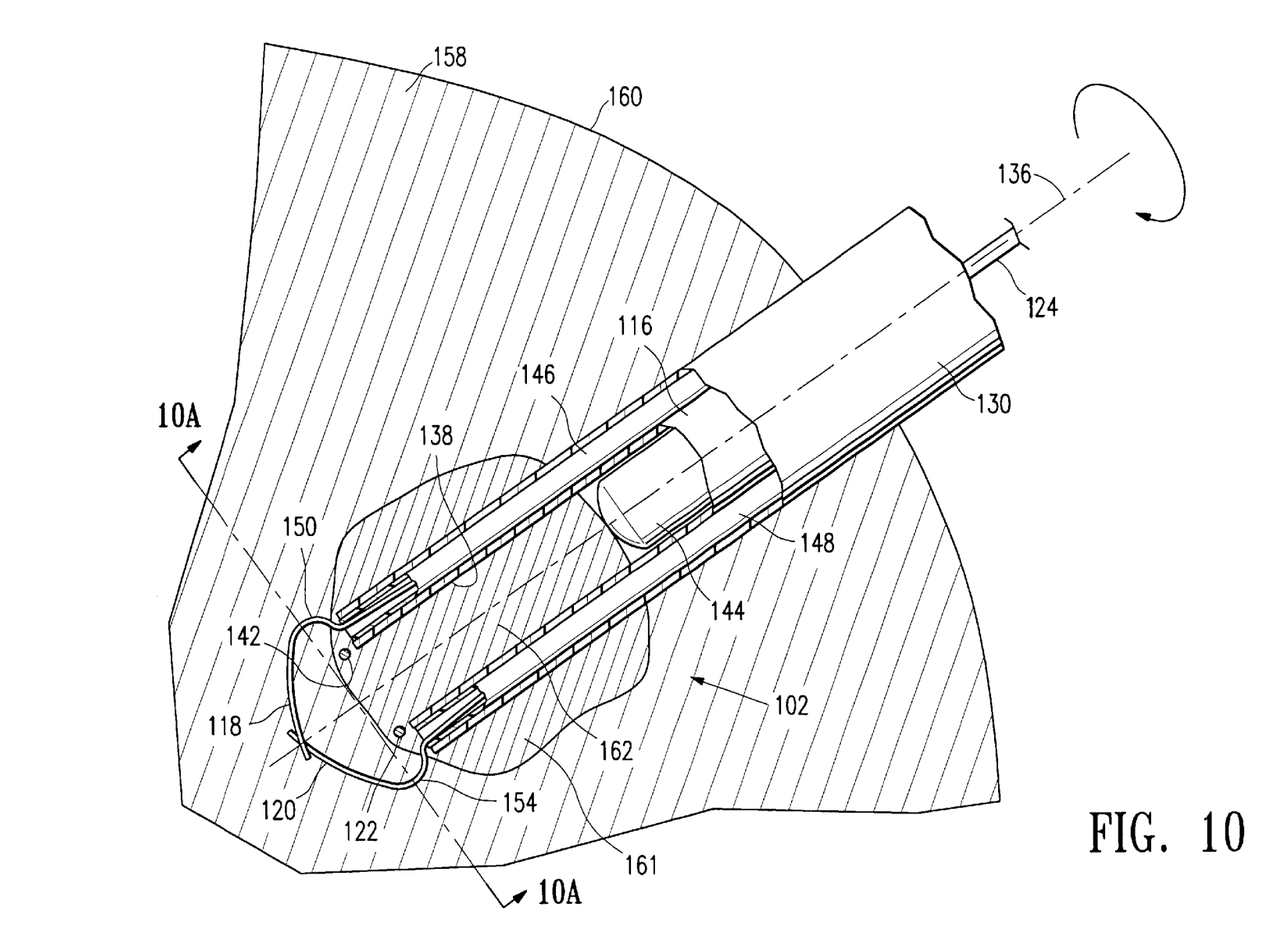
FIG. 10 is a cross-sectional view of the cannula assembly illustrated in FIG. 2, showing the pair of opposing retractable electrodes in the extended position and the cannula assembly positioned inside of the tissue of the patient with a tissue sample located in the cannula assembly.
Figure 10A:
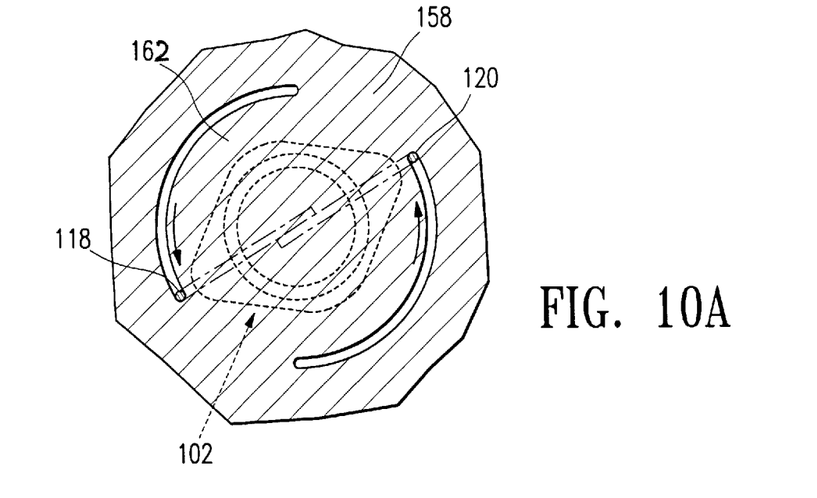
FIG. 10A shows the cannula assembly of FIG. 10 taken along lines 10A—10A illustrating rotation of the cannula assembly about the longitudinal axis of the cannula in order to separate the tissue sample contained within the cannula.
Figure 11:
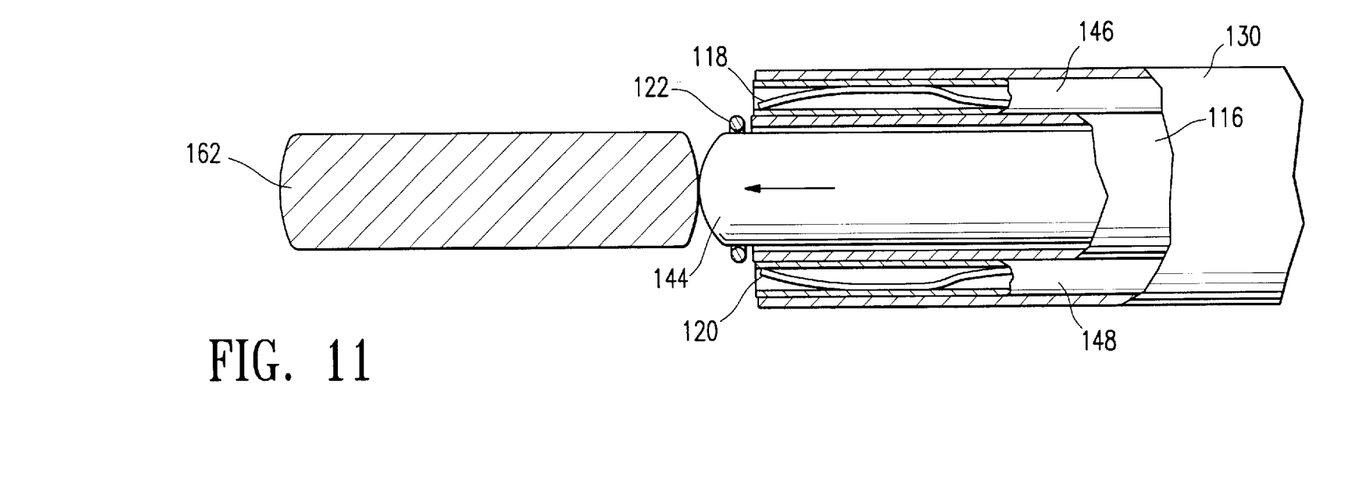
FIG. 11 is a cross-sectional view of the cannula assembly illustrated in FIG. 2, showing the pair of opposing retractable electrodes in the retracted position with a tissue sample ejected from the cannula assembly by a dilator.
Figure 12:
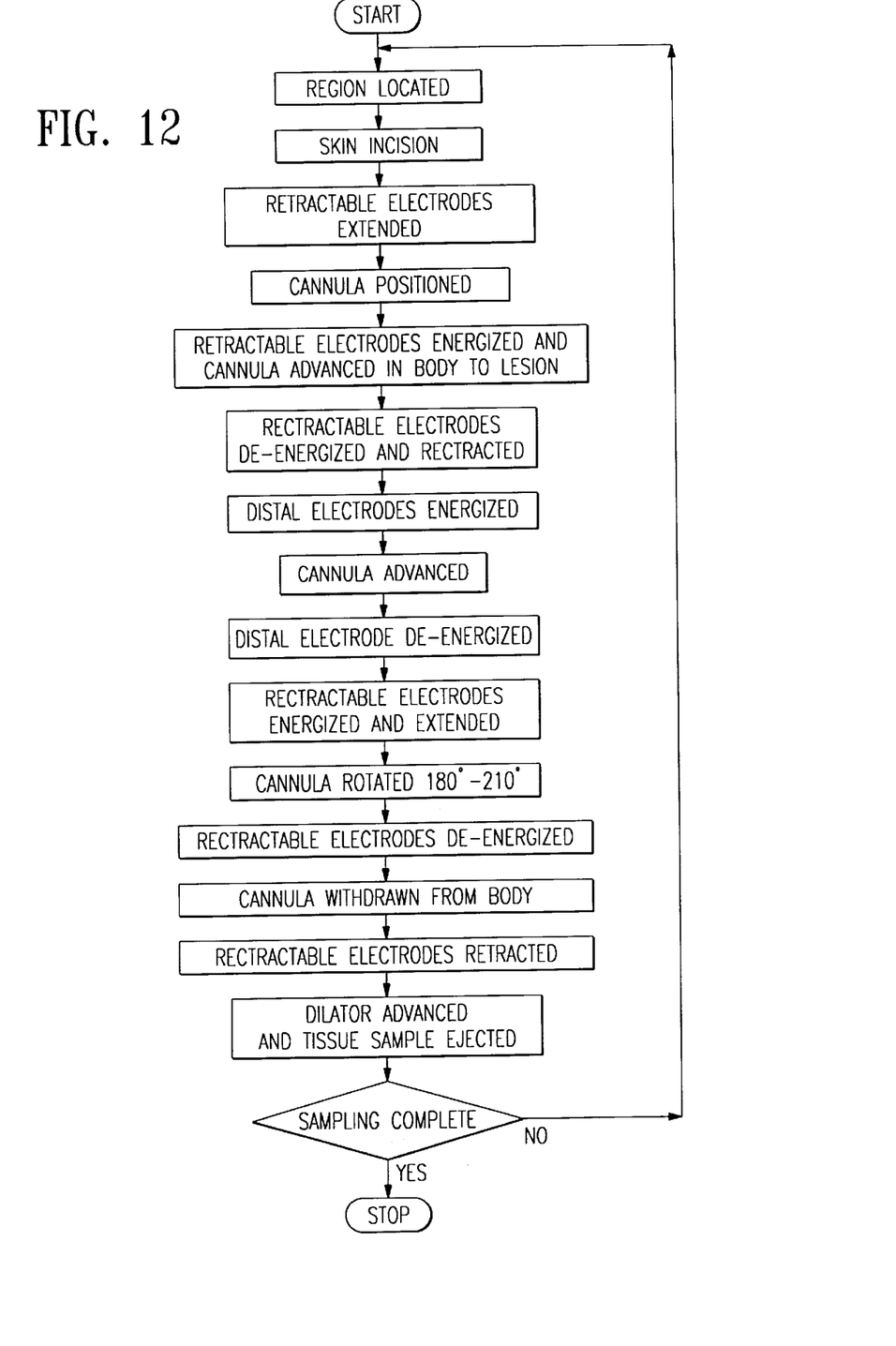
FIG. 12 is an illustration of an exemplary process according to the present invention.

When an adequate tissue sample 162 is located in the tissue lumen 138, the cannula assembly 102 is stopped and the RF energy to the distal electrode 122 is turned off as well as the optional vacuum source 108. The retractable electrodes 118 and 120 are then energized with RF energy and are extended. As shown in FIG. 10, the cannula assembly 102 is rotated approximately 180 to 270 degrees to separate the tissue sample 162 from the body of the patient. Preferably, the cannula assembly 102 is rotated approximately 180 to 225 degrees. More preferably, the cannula assembly 102 is rotated approximately 180 to 210 degrees. The retractable electrodes 118 and 120 are then de-energized. The cannula assembly 102 is then removed from the tissue 158 with the retractable electrodes 118 and 120 being fully extended to help secure the tissue sample 162 in the tissue lumen 138. The retractable electrodes 118 and 120 are then retracted and the dilator 144 is advanced through the tissue lumen 138 to eject the tissue sample 162 from the cannula 116. The tissue sample is then placed in a container. The retractable electrodes 118 and 120 are then extended and positioned for another biopsy if another tissue sample is required. If tissue sampling is complete, post-procedural bandaging is performed.

The process described above may be assisted by computer logic that may be implemented in controlling the vacuum source 108, motor driver 112, and RF generator 106 by a programmable logic controller (not illustrated), a general purpose digital computer in communication with a memory element containing computer readable instructions which embody the control logic (not illustrated), application specific integrated circuit (ASIC) (not illustrated), or discrete digital signal processing (DDSP) (not illustrated).

While the invention has been described in detail with reference to preferred embodiments thereof, it will be apparent to one skilled in the art that various changes can be made, and equivalents employed, without departing from the scope of the invention.

What is claimed is:

1. A tissue acquisition device for retrieving tissue samples from a patient, comprising:
   a cannula having a proximal end, a distal end, a longitudinal axis extending between the proximal and distal ends, and a tissue lumen extending along the longitudinal axis from the proximal end toward the distal end;
   a distal electrode which has a lumen that is substantially aligned with the cannula tissue lumen and which is secured to the distal end of the cannula; and
   at least two retractable electrodes extendable distally from the distal end of the cannula.

2. The tissue acquisition device in accordance with claim 1, wherein the distal electrode and the cannula are generally circular in cross sectional shape and the lumen of the distal electrode is substantially coaxial with the cannula tissue lumen.

3. The tissue acquisition device in accordance with claim 1, further comprising at least one distal electrode support that extends generally parallel to the cannula longitudinal axis along an outer surface of the cannula from generally the cannula proximal end to generally the cannula distal end, the distal electrode support having a distal end in electrical contact with the distal electrode.

4. The tissue acquisition device in accordance with claim 3, further comprising a plurality of distal electrode supports that extend generally parallel to the cannula longitudinal axis along an outer surface of the cannula from generally the cannula proximal end to generally the cannula distal end, each of the distal electrode supports having distal ends in electrical contact with the distal electrode.

5. The tissue acquisition device in accordance with claim 4, further comprising a sheath covering the cannula, the retractable electrode and the distal electrode supports and extending generally from the cannula proximal end to the cannula distal end.

6. The tissue acquisition device in accordance with claim 1, further comprising a dilator movably positioned in the cannula tissue lumen.

7. The tissue acquisition device in accordance with claim 1, wherein the at least two retractable electrodes comprise a pair of opposing retractable electrodes located externally of the cannula and extending generally from the proximal end of the cannula to generally the distal end of the cannula when in a retracted position.

8. The tissue acquisition device in accordance with claim 7, wherein the distal electrode and the retractable electrodes are electrically connected to an energy source.

9. The tissue acquisition device in accordance with claim 8, wherein the energy source is an RF energy source.

10. The tissue acquisition device in accordance with claim 7, wherein the retractable electrodes are disposed in a housing when retracted and have a first configuration when retracted and a second configuration when distally extended from the housings which extends at least partially towards the longitudinal axis of the cannula.

11. The tissue acquisition device in accordance with claim 10, wherein the retractable electrodes in the second configuration extend distally of the distal electrode and cross the longitudinal axis of the cannula.

12. The tissue acquisition device in accordance with claim 10, wherein the retractable electrodes each have an apex that extends radially farther from the longitudinal axis of the cannula than an outer surface of the cannula when in the second configuration.

13. The tissue acquisition device in accordance with claim 1 wherein the cannula tissue lumen further comprises a lubricious coating on an inner surface thereof.

14. A system for sampling tissue from a patient, comprising:
   a RF energy generator capable of generating RF energy; and
   a tissue acquisition device in accordance with claim 1, wherein the distal electrode and the at least two retractable electrodes of the tissue acquisition device are in electrical communication with the RF energy generator.

15. The system in accordance with claim 14, further comprising a vacuum source in fluid communication with the cannula tissue lumen.

16. The system in accordance with claim 14 wherein the at least two retractable electrodes comprise a pair of opposing retractable electrodes having a first configuration when retracted, a second configuration when extended in which the retractable electrodes extend distally of the distal electrode and cross the longitudinal axis of the cannula and an apex that extends radially farther from the longitudinal axis of the cannula than an outer surface of the cannula when in the second configuration.

17. A method of sampling tissue from a patient, comprising:
   (a) providing a tissue acquisition device having:
      a cannula having a proximal end, a distal end, a longitudinal axis extending between the proximal and distal ends, and a tissue lumen extending along the longitudinal axis from the distal end of the cannula;
      a distal electrode which has a lumen that is substantially aligned with the cannula tissue lumen and which is secured to the distal end of the cannula; and
      at least two retractable electrodes extendable distally from the distal end of the cannula; p1 (b) inserting the cannula into target tissue of a patient with the distal electrode energized such that at least a portion of the target tissue enters the cannula tissue lumen;
   (c) extending the at least two retractable electrodes;
   (d) energizing the at least two retractable electrodes; and
   (e) separating the target tissue within the cannula tissue lumen by rotating the cannula and the at least two retractable electrodes through the tissue of the patient with the at least two retractable electrodes energized.

18. The method of sampling tissue from a patient in accordance with claim 17, wherein the distal electrode and the at least two retractable electrodes are energized by applying RF energy to the electrodes.

19. The method of sampling tissue from a patient in accordance with claim 17, further comprising aspirating a tissue sample through the tissue lumen of the cannula.

20. The method of sampling tissue from a patient in accordance with claim 17, wherein the at least two retractable electrodes comprise a pair of opposing retractable electrodes extending generally from the proximal end of the cannula to generally the distal end of the cannula when in a retracted position, and further comprising extending the two opposing retractable electrodes from the cannula and energizing the two opposing retractable electrodes prior to separating the target tissue within the cannula tissue lumen from the surrounding tissue.

21. The method of sampling tissue from a patient in accordance with claim 20, wherein the two opposing retractable electrodes have a first configuration when retracted, a second configuration when extended in which the retractable electrodes extend distally of the distal electrode and overlap each other and an apex that extends radially farther from the longitudinal axis of the cannula than an outer surface of the cannula.

22. The method of sampling tissue from a patient in accordance with claim 20 further comprising energizing the opposing retractable electrodes by applying RF energy to the retractable electrodes.

23. The method of sampling tissue from a patient in accordance with claim 20, wherein the cannula is rotated at least 180 degrees to separate the tissue sample from the patient.

24. The method sampling tissue from a patient in accordance with claim 20, wherein the cannula is rotated approximately 180 to 270 degrees to separate the tissue sample from the patient.

25. The method of sampling tissue from a patient in accordance with claim 20, wherein the cannula is rotated approximately 180 to 210 degrees to separate the tissue sample from the patient.

26. The method of sampling tissue from a patient in accordance with claim 17, wherein at least three retractable electrodes are extended into the tissue of a patient.

* * * * *